(12) United States Patent
Wilsberg

(10) Patent No.: US 6,444,023 B1
(45) Date of Patent: *Sep. 3, 2002

(54) LIQUID LAUNDRY STARCH CONCENTRATE

(75) Inventor: Heinz-Manfred Wilsberg, Duesseldorf (DE)

(73) Assignee: Henkel Ecolab GmbH & Co, OHG, Dusseldorf (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/214,098
(22) PCT Filed: Jun. 20, 1997
(86) PCT No.: PCT/EP97/03221
§ 371 (c)(1), (2), (4) Date: Dec. 28, 1998
(87) PCT Pub. No.: WO98/00599
PCT Pub. Date: Jan. 8, 1998

(30) Foreign Application Priority Data

Jun. 28, 1996 (DE) .......................................... 196 25 828

(51) Int. Cl.⁷ .................... C09D 105/00; C09D 103/02; C09D 7/12
(52) U.S. Cl. ................................................. 106/205.6
(58) Field of Search .......................... 106/205.6, 214.1, 106/214.2

(56) References Cited

U.S. PATENT DOCUMENTS 3,692,552 A   9/1972   Rueggeberg ................ 106/208

FOREIGN PATENT DOCUMENTS

DE   19 40 655      9/1986
WO   WO86/05509    9/1986

OTHER PUBLICATIONS

Dr. Otto–Albrecht Neumueller, "Roempps Chemie–Lexikon, Achte, neubearbeitete und erweiterte Auflage",Stuttgart, (1987) no month provided pp. 3438–3439.

J. Biochemical and Microbiological Technology & Engineering vol. III (1961) no month provided pp. 51–63 "Production of Polysaccharide with Xanthomonas Campestris".

Primary Examiner—David Brunsman
(74) Attorney, Agent, or Firm—Merchant & Gould P.C.

(57) ABSTRACT

A process for preserving a liquid laundry starch concentrate containing starch or starch derivatives suspended in an aqueous xanthan solution by adding to the concentrate ethanol and a quaternary ammonium compound corresponding to general formula (I):

$$R^1R^2(CH_3)_2N^+A^- \qquad (1)$$

In which $R^1$ and $R^2$ independently of one another represent a linear or branched alkyl group containing 8 to 18 carbon atoms and $A^-$ is a charge equalizing anion.

22 Claims, No Drawings

LIQUID LAUNDRY STARCH CONCENTRATE

This application is a 371 of PCT/EP97/03221 filed Jun. 20, 1997.

BACKGROUND OF THE INVENTION

1. Field of the Invention

This invention relates to liquid laundry starch concentrates, more particularly for use in institutional laundries, which contain an aqueous suspension of starch and a certain preservative system and to the use of the preservative system in liquid starch concentrates.

Starch-containing preparations are generally used for starching or finishing laundry. They are used either as a "boil-up" of initially non-gelatinized starch or as solution of pregelatinized starch or as a suspension of non-gelatinized starch which only gelatinizes on the laundry on exposure to relatively high temperatures, for example during ironing or mangling, and which produces the required stiffness, for example in the case of table linen. Corresponding preparations may also contain other typical ingredients of so-called laundry aftertreatment preparations which improve, for example, the so-called feel or the ironing behavior of the laundry. To make it easier to add in the right quantity and also to handle, it is of advantage to use laundry starch in liquid form. This applies in particular to the use of laundry starch in institutional laundries where predissolved active substances, so-called stock liquors, are normally introduced automatically by pumps into the washing drums or into the particular section of a multiple-compartment batch washing machine. From this arises one of the requirements which the preparation according to the invention is expected to satisfy, i.e. its ability to form a stock liquor or, in other words, its stability in storage after dilution with water. This applies both to the physical stability, i.e. the avoidance of phase separation, such as the sedimentation of starch, and to the microbiological stability of the suspensions. Preparations which contain starch—a readily biodegradable material—are susceptible to infestation by microorganisms. This problem is aggravated by the need arising in institutional laundries to use stock liquors which are normally stored for several days in storage containers and which are added from those containers. Even though microbial infestation may not impair the effectiveness of the starch suspensions, it is unacceptable, particularly in the case of germs to which human beings are susceptible, because of course the laundry starch remains on the treated textile and comes into contact with human beings.

2. Disclosure of Related Art

It is known that the separation of starch from the suspension can be avoided by using a so-called carrier liquor, for example an aqueous solution of carboxymethyl cellulose. However, in order to keep a large amount of starch suspended, as required by the user, the concentration of carboxymethyl cellulose has to be so high that the handling of the laundry starch concentrate is complicated by the thickening effect of the carboxymethyl cellulose. If a starch suspension pregelatinized by brief heating, for example to between 40 and 60° C., is used, difficulties arise out of the fact that, where carboxymethyl cellulose is used, the preparation thickens considerably after only a short time.

German patent 1 940 655 describes starch suspensions which contain a solution of xanthan gum and/or water-soluble derivatives of xanthan gum as their aqueous phase. The starch is effectively prevented from sedimenting in this way.

To increase stability to microorganism infestation, it is proposed in the cited document to use conventional disinfectants, such as formaldehyde. Since disinfectants such as formaldehyde also remain on the starched laundry, there is again a risk of their coming into contact with. and affecting the user. Consequently, formaldehyde and other aldehydes, phenols and substances which release active chlorine cannot be used despite their favorable antimicrobial activity.

Accordingly, the problem addressed by the present invention was to provide a preservative for laundry starch concentrates which, on the one hand, would reliably prevent microbial infestation of the laundry starch concentrate and the aqueous stock liquor prepared therefrom and which, on the other hand, would not remain on the starched laundry in quantities or activities likely to affect the user.

DESCRIPTION OF THE INVENTION

This problem has largely been solved by the use of a combination of ethanol and a quaternary ammonium compound corresponding to general formula (I):

$$R^1R^2(CH_3)_2N^+A^- \qquad (I)$$

in which $R^1$ and $R^2$ independently of one another represent a linear or branched alkyl group containing 8 to 18 carbon atoms, more particularly 8 to 10 carbon atoms, and $A^-$ is a charge-equalizing anion, such as halide (for example chloride, bromide, iodide, fluoride), methosulfate or ethosulfate, for preserving aqueous laundry starch concentrates which contain starch or starch derivatives suspended in an aqueous xanthan solution.

In the combination to be used in accordance with the invention, the ratio by weight of the components ethanol to quaternary ammonium compound is preferably 5,000:1 to 1:1 and, more preferably, 400:1 to 10:1. The combination to be used in accordance with the invention is preferably present in liquid form and may contain other ingredients emanating, for example, from the particular form in which the components are supplied. Thus, besides water, ethanol often contains so-called denaturing agents, such as methyl ethyl ketone, while quaternary ammonium compounds are commercially available in the form of preparations which, besides water, contain other lower alcohols than ethanol, for example isopropanol.

The combination to be used in accordance with the invention is preferably used in quantities of 1 part by weight to 10 parts by weight and more preferably in quantities of 2 parts by weight to 8 parts by weight, based on 100 parts by weight of the liquid laundry starch concentrate as a whole, for preserving the concentrate.

The present invention also relates to a liquid laundry starch concentrate which contains starch or starch derivatives suspended in an aqueous xanthan solution and which is characterized in that it contains ethanol and a quaternary ammonium compound corresponding to general formula (I):

$$R^1R^2(CH_3)_2N^+A^- \qquad (I)$$

in which $R^1$ and $R^2$ independently of one another represent a linear or branched alkyl group containing 8 to 18 carbon atoms, more particularly 8 to 10 carbon atoms, and $A^-$ is a charge-equalizing anion, such as halide (for example chloride, bromide, iodide, fluoride), methosulfate or ethosulfate. Ethanol is present in the preparations according to the invention in quantities of preferably 1% by weight to 10% by weight and, more preferably, 2% by weight to 8% by weight whereas the quaternary ammonium compound corresponding to general formula I is present in quantities of preferably 0.002% by weight to 0.5% by weight and, more preferably, 0.02% by weight to 0.2% by weight. In the quaternary ammonium compounds corresponding to general formula I, $R^1$ is preferably identical with $R^2$. Preferred alkyl groups $R^1$ and $R^2$ are decyl groups, more particularly n-decyl groups. Ethanol and the quaternary ammonium compound of general formula I may be incorporated in the preparations according to the invention in the form of the combination to be used in accordance with the invention or separately.

The starch used may be selected from any of the starches and starch derivatives present in granular or powder form, for example corn starch, rice starch, potato starch and/or tapioca starch. It is preferably present in native form although it may also be thermally, hydrolytically or oxidatively degraded. Starches in the context of the present invention also include any starch derivatives which are largely insoluble in cold water and which gelatinize in hot water. Starch is present in the preparations according to the invention in quantities of preferably 10% by weight to 50% by weight and more preferably 20% by weight to 45% by weight.

For stabilization against the sedimentation of starch, the aqueous preparations according to the invention contain water-soluble xanthan which is commercially available, for example, under the product names of Keizan®, Rhodopol®, Ketrol® or Rheozan®. Xanthan is understood to be a polysaccharide corresponding to that produced by the bacterial strain Xanthomas campestris from aqueous solutions of glucose or starch (J. Biochem. Microbiol. Technol. Engineer. Vol. III (1961), pages 51 to 63). It consists essentially of glucose, mannose, glucuronic acid and acetylation products thereof and, in addition, contains small quantities of chemically bound pyruvic acid. Water-soluble xanthan derivatives obtainable, for example, by alkoxylation with, for example, ethylene oxide, propylene oxide and/or butylene oxide, by alkylation with, for example, methyl halides and/or dimethyl sulfate, by acylation with carboxylic acid halides or by saponifying deacetylation may also be used. Xanthan is present in preparations according to the invention in quantities of preferably 0.1% by weight to 2% by weight and, more preferably, 0.2% by weight to 1.5% by weight. It makes a critical contribution to the viscosity of the laundry starch concentrates according to the invention which, at room temperature, is preferably in the range from 500 mPa·s to 10,000 mPa·s and more preferably in the range from 1,000 mPa·s to 6,000 mPa·s. A particular advantage of using xanthan is that there is very little change in viscosity over a broad temperature range of −5° C. to 40° C. and, even beyond this temperature range, values in the preferred viscosity range mentioned are reversibly re-established when the preparation is returned to room temperature.

The liquid laundry starch concentrates according to the invention may additionally contain any of the ingredients normally encountered in such preparations, including for example lubricants, anionic and/or nonionic surfactants, water-miscible solvents, for example emulsifiers, such as ethylene glycol and/or glycerol, lustering agents, such as borax, and dyes and perfumes. Water is present in the preparations according to the invention in quantities of preferably 40% by weight to 90% by weight and, more preferably, 45% by weight to 80% by weight.

To use the liquid laundry starch, a concentrate according to the invention may be diluted with water to such an extent that a ready-to-use solution containing 0.5 g/l to 10 g/l of starch is formed. This solution may be used in the home either by hand or as a rinsing solution in the rinse cycle of a conventional washing machine. Where it is used in institutional laundries, the preparation according to the invention is added to the final rinse bath, preferably in quantities of 2 to 30 g per kilogram of dry laundry.

EXAMPLES

A laundry starch concentrate M1 with the composition shown in Table 1 below was prepared simply by mixing the ingredients. To this end, the water was introduced first and heated to about 80° C., after which the PEG triglyceride, borax and glycerol were stirred in and, after cooling to below 30° C., ethanol diluted with water was added, the corn starch was stirred in, an aqueous mixture of xanthan and QUAT was added and the whole was mixed with the perfume. The preparation had a pH value of 7.9 and was stable in storage for at least 24 hours at temperatures of −10° C. to 50° C. without significant sedimentation of the starch, its viscosity (as measured at room temperature) undergoing hardly any change.

TABLE 1

| Composition (% by weight) of laundry starch concentrates | |
|---|---|
| Concentrate | M1 |
| Corn starch | 30 |
| Xanthan | 0.4 |
| Ethanol | 4.8 |
| QUAT[a] | 0.05 |
| PEG triglyceride | 2.25 |
| Glycerol | 5 |
| Borax | 2.5 |
| Perfume | 0.45 |
| Water | to 100 |
| Viscosity[b] | 3,000 |

[a]didecyl dimethyl ammonium chloride
[b]in mPa · s, as measured at room temperature using a Brookfield RVT rotational viscosimeter (spindle No. 3, 20 r.p.m.).

What is claimed is:

1. A liquid laundry starch concentrate comprising starch or starch derivatives suspended in an aqueous xanthan solution wherein said concentrate contains ethanol and a quaternary ammonium compound corresponding to general formula (1):

$$R^1R^2(CH_3)_2N^+A^- \qquad (1)$$

in which $R^1$ and $R^2$ represent n-decyl groups, and $A^-$ is charge-equalizing anion.

2. A concentrate as in claim 1 wherein said starch is selected from the group consisting of corn starch, rice starch, potato starch and tapioca starch and is present in native form or in thermally, hydrolytically or oxidatively degraded form.

3. A concentrate as in claim 1 wherein said starch or starch derivatives are present in a quantity of 10% by weight to 50% by weight, based on the weight of said concentrate.

4. A concentrate as in claim 1 wherein said xanthan is present a quantity of 0.1% by weight to 2% by weight, based on the weight of said concentrate.

5. A concentrate as in claim 1 wherein said ethanol is present in a quantity of 1% by weight to 10% by weight and, said quaternary ammonium compound is present in a quantity of 0.002% by weight to 0.5% by weight, based on the weight of said concentrate.

6. A concentrate as in claim 1 containing 40% by weight to 90% by weight of water, based on the weight of said concentrate.

7. A concentrate as in claim 1 having a viscosity at room temperature of 500 mPa·s to 10,000 mPa·s.

8. A concentrate as in claim 1 wherein A⁻ is a charge-equalizing anion selected from the group consisting of a halide, methosulfate and ethosulfate.

9. A concentrate as in claim 1 wherein said ethanol and said quaternary ammonium compound are present in a weight ratio of 5,000:1 to 1:1.

10. A concentrate as in claim 1, wherein the quaternary ammonium compound comprises didecyl dimethyl ammonium halide.

11. A concentrate as in claim 10, wherein the didecyl dimethyl ammonium halide comprises didecyl dimethyl ammonium chloride.

12. The process of preserving a liquid laundry starch concentrate containing starch or starch derivatives suspended in a aqueous xanthan solution, comprising adding to said concentrate ethanol and quaternary ammonium compound corresponding to general formula (1):

$$R^1R^2(CH_3)_2N^+A^- \qquad (1)$$

in which $R^1$ and $R^2$ represent n-decyl groups, and $A^-$ is a charge-equalizing anion.

13. A process as in claim 12 wherein said starch is selected from the group consisting of corn starch, rice starch, potato starch and tapioca starch and is present in native form or in thermally, hydrolytically or oxidatively degraded form.

14. A process as in claim 12 wherein said starch or starch derivatives are present in a quantity of 10% by weight to 50% by weight, based on the weight of said concentrate.

15. A process as in claim 12 wherein said xanthan is present in a quantity of 0.1% by weight to 2% by weight based on the weight of said concentrate.

16. A process as in claim 12 wherein said ethanol is present in quantity of 1% by weight to 10% by weight and said quaternary ammonium compound is present in a quantity of 0.002% by weight to 0.5% by weight, based on the weight of said concentrate.

17. A process as in claim 12 wherein said concentrate contains 40% by weight to 90% by weight of water, based on the weight of said concentrate.

18. A process as in claim 12 wherein said concentrate has a viscosity at room temperature of 500 mPa·s to 10,000 mPa·s.

19. A process as in claim 12 wherein A⁻ is a charge-equalizing anion selected from the group consisting of a halide, methosulfate and ethosulfate.

20. A process as in claim 12 wherein said ethanol and said quaternary ammonium compound are present in a weight ratio of 5,000:1 to 1:1.

21. A process as in claim 12, wherein quaternary ammonium compound comprises didecyl dimethyl ammonium halide.

22. A process as in claim 21, wherein the didecyl dimethyl ammonium halide comprises didecyl dimethyl ammonium chloride.

* * * * *

UNITED STATES PATENT AND TRADEMARK OFFICE
CERTIFICATE OF CORRECTION

PATENT NO. : 6,444,023 B1  
DATED : September 3, 2002  
INVENTOR(S) : Heinz-Manfred Wilsberg It is certified that error appears in the above-identified patent and that said Letters Patent is hereby corrected as shown below:

Column 3,
Line 27, "Keizan" should be -- Kelzan --

Signed and Sealed this

Fourth Day of March, 2003

JAMES E. ROGAN
*Director of the United States Patent and Trademark Office*